United States Patent [19]

Carlson

[11] Patent Number: 4,888,133
[45] Date of Patent: Dec. 19, 1989

[54] NEW ANTIOXIDANT SURFACTANTS

[75] Inventor: Thommy Carlson, Helsingborg, Sweden

[73] Assignee: Nestec S.A., Vevey, Switzerland

[21] Appl. No.: 149,360

[22] Filed: Jan. 28, 1988

Related U.S. Application Data

[62] Division of Ser. No. 794,519, Nov. 4, 1985, Pat. No. 4,745,199.

[30] Foreign Application Priority Data

Nov. 29, 1984 [EP] European Pat. Off. ............ 84114490

[51] Int. Cl.$^4$ ............................................. C09K 15/06
[52] U.S. Cl. ........................... 252/400.61; 252/400.62; 252/407; 426/546
[58] Field of Search ........... 549/315; 252/407, 400.61, 252/400.62; 426/546

[56] References Cited

U.S. PATENT DOCUMENTS

| | | | |
|---|---|---|---|
| 2,454,748 | 11/1948 | Weisblat et al. | 549/315 |
| 2,454,749 | 11/1948 | Wise | 549/315 X |
| 2,995,495 | 8/1961 | Pancrazio et al. | 549/315 X |
| 3,151,127 | 9/1964 | Spanel | 549/315 |
| 4,745,199 | 5/1988 | Carlson | 549/315 |

FOREIGN PATENT DOCUMENTS 222078 of 1983 Japan.

OTHER PUBLICATIONS

Paul A. Seib et al, Editors, Advances in Chemistry Series 200, Ascorbic Acid: Chemistry, Metabolism, and Uses, (1982), pp. 534–537.

*Primary Examiner*—John F. Terapane
*Assistant Examiner*—Valerie D. Fee
*Attorney, Agent, or Firm*—Vogt & O'Donnell

[57] ABSTRACT

Antioxidant compositions are provided by compounds having the general formula:

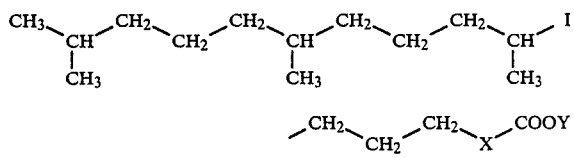
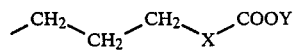

wherein X is an alkylene radical containing from 1 to 3 carbon atoms and Y is a residue of L-ascorbic acid having the formula:

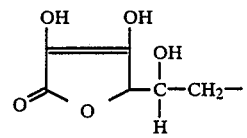

or a residue of D-isoascorbic acid having the formula:

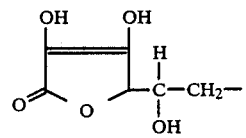

and the corresponding salts thereof in an aqueous medium wherein sufficient water is present for inducing a lamellar liquid crystalline phase.

7 Claims, No Drawings

ANTIOXIDANT SURFACTANTS

CROSS REFERENCE TO RELATED APPLICATIONS

This is a divisional application of Application Ser. No. 794,519, filed Nov. 4, 1985, now U.S. Pat. No. 4745199.

BACKGROUND OF THE INVENTION

The present invention relates to novel chemical compounds with surfactant properties, more particularly to ascorbic acid esters of saturated branched long chain aliphatic acids.

SUMMARY OF THE INVENTION

The present invention provides a compound having the general formula:

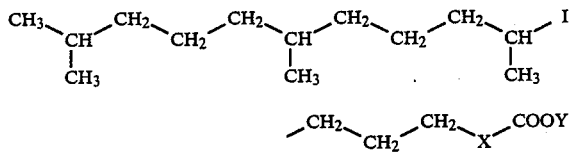

wherein X is an alkylene radical containing from 1 to 3 carbon atoms and Y is a residue of L-ascorbic acid having the formula:

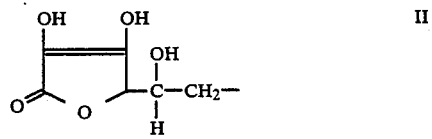

or a residue of D-isoascorbic acid having the formula:

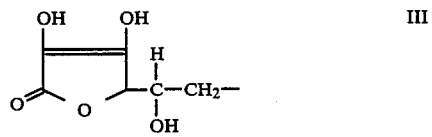

and the corresponding salts thereof.

The alkylene radical X may, for instance, be methylene but is preferably an isopropylene radical having the formula:

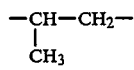

DETAILED DESCRIPTION OF THE INVENTION

The compound of formula I may conveniently be prepared by conventional procedures for preparing analogous compounds, for instance, by esterifying the appropriate ascorbic acid with the appropriate acid under acid conditions to form a saturated branched chain ester compound. Conveniently, the reaction is carried out in the presence of a concentrated mineral acid such as $H_2SO_4$ with cooling. Afterwards, the desired compound may be obtained by extraction with a polar or apolar organic solvent such as ether.

In the preparation of a compound of formula I where X is an isopropylene radical having the formula IV the ascorbic acid is esterified with phytanic acid. The phytanic acid may be prepared from phytol, for example, by the hydrogenation of the double bond and the oxidation of the alcohol function. Phytol is a branched hydrocarbon containing 20 carbon atoms; it is a diterpene and is obtained mainly from chlorophyll.

In the preparation of a compound of formula I where X is a methylene radical, the ascorbic acid is esterified with an acid which may be prepared from isophytol, for example, by hydrogenating the double bond and oxidising the alcohol function. Isophytol has been found in the oil extract of jasmin.

The salts of the compounds of general formula I may be, for example, the alkali and alkaline earth metal salts such as the sodium, potassium, calcium and magnesium salts. They may be prepared by conventional methods, for instance, by adding a metal propionate to an ethanolic solution of the compound of general formula I or by adding a metal methoxide to an acetone solution of the compound of general formula I.

The compounds of the general formula I and their salts have surfactant properties; they form liposomes in water, which are more stable towards ionic strength than liposomes based on lecithin, and they are also stable towards hydrocarbon chain oxidation. They may be used as antioxidants for oxidation sensitive foodstuffs, especially foods having a high water content. The problem with treating such hydrophilic or "wet" foodstuffs with antioxidants is that hydrophobic antioxidants such as butylhydroxytoluene, butylhydroxyanisole, tocopherol or ascorbyl palmitate cannot reach the entire bulk of the food, while water-soluble antioxidants such as ascorbic acid diffuse so slowly that such a treatment is not practical.

A more practical approach would be to produce a film of oxidation on the external surface of the foodstuff. However, the common antioxidants will not form a continuous film but crystallise on the surface as the solvent evaporates and thus the antioxidant effect is not satisfactory.

We have found, surprisingly, that the compounds of general formula I are excellent antioxidants in an aqueous medium because they form a lamellar liquid crystalline phase in water which will spread as bimolecular layers on the surfaces of the hydrophilic foodstuff to give a film which gives a very efficient protection against antioxidation. The lamellar phase is present when the water content of the aqueous medium is above 10% when containing the free acid and above 5% when containing the salt on a weight/weight basis.

Accordingly, the present invention also provides an antioxidant vehicle composition comprising a compound of the general formula I and at least sufficient water to induce a lamellar liquid crystalline phase.

Preferably, the amount of compound of the general formula I is from 0.01% to 1.0% by weight and especially from 0.05% to 0.5% by weight based on the total weight of the composition.

The present invention also provides a process for inhibiting oxidation of a foodstuff susceptible to oxidation wherein the foodstuff is treated with a composition comprising an effective oxidation inhibiting amount of a compound having the general formula I in an aqueous medium containing at least 10% by weight of water based on the total weight of the composition.

The present invention also provides a composition comprising a foodstuff susceptible to oxidation and an effective oxidation inhibiting amount of a compound of the general formula I in the form of a film on the surface of the foodstuff.

Foodstuffs which may advantageously be protected against oxidation by means of the compounds having the general formula I are, for example, carrots and foodstuffs containing fats, such as ham.

Compounds of the general formula I which are valuable antioxidants are those in which the alkylene radical X is methylene and especially those in which the alkylene radical X is an isopropylene radical having the formula IV, for example, 6-0-Phytanoyl-L-ascorbic acid.

The saturated branched chain compounds having the general formula I are liquid at temperatures above $-20°$ C. and are stable. The liquid chain is a requirement for the formation of the lamellar liquid crystalline phase. These compounds thus have advantages over the corresponding saturated straight chain compounds and the unsaturated branched chain compounds; the saturated straight chain compounds are solid up to about 90° C. and although the unsaturated branched chain compounds are liquid above about 0° C., they are unstable owing to oxidation.

The following Examples further illustrate the present invention.

EXAMPLES

Example 1

To a flask containing 3.52 g (20 millimoles) of L-ascorbic acid, 20 ml of concentrated $H_2SO_4$ (95–97%, Merck) were slowly added under stirring and cooling at 0° C. After 20 minutes stirring at room temperature, 6.4 g (20.5 millimoles) of phytanic acid, prepared from phytol by successive catalytic hydrogenation of the double bond and oxidation of the alcohol function, were added dropwise. After 3 hours, the reaction mixture was poured on ice and extracted with three portions containing 30 ml of ether. The combined ethereal extracts were dried over $Na_2SO_4$ and concentrated under vacuum. The residue was purified by column chromatography (MN-Polyamide CC6, chloroform). 2.8 g of 6-0-Phytanoyl-L-ascorbic acid were isolated as an oil, i.e., a 38% yield. Upon drying under high vacuum a glassy solid was obtained having a purity of at least 95%. The spectroscopic data are as follows:

CI MS ($NH_3$): m/z: 488 ([M+$NH_4$]+); 470 (M+); 430; 330 ([Phytanoic acid+$NH_4$]+)

$^{13}$C-NMR ($CDCl_3$): δ(ppm): 173.7(C-1'); 172.5(C-1); 152.3(C-3); 119.1(C-2); 76.1(C-4); 67.9(C-5); 63.9(C-6); 41.7(C-2'); 39.4(C-14'); 37.5/37.3(C-4', 6', 8', 10', 12'); 32.8 (C-7', 11'); 30.4(C-3'); 28.0(C-15'), 24.8/24.5(C-5', 9', 13'); 22.7(C-16', 15-Me); 19.7(3'-, 7'-, 11'-Me).

Example 2

Cut and blanched carrots of size $10 \times 10 \times 3$ mm$^3$ were dipped into a 0.1% weight/weight dispersion of 6-0-Phytanoyl-L-ascorbic acid in distilled water for 10 minutes at 22° C. A control was made by dipping carrots of the same size for the same time and at the same temperature in the same amount of distilled water not containing any antioxidant. The treated carrots were frozen and freeze-dried.

The dry carrot pieces having a water activity (Aw) of less than 0.10 were stored at 37° C. in sealed glass jars for the periods of time shown in Table I below and the effects of storage were evaluated by observing changes in smell and colour. Oxidation leads to a smell of hay and carotene degradation leads to increased whiteness.

TABLE I

| Storage time (days) | 18 | 40 | 60 |
|---|---|---|---|
| Example 1 | No smell of hay change | Slight smell of hay No colour change | Smell of hay Slight increase of whiteness |
| Control | Smell of hay No white spots | Strong smell of hay Many white spots | Strong smell of hay all carrots were white/yellow in colour |

After 180 days significant more carotene colour could be observed for the carrots treated with antioxidant.

It can be seen that the new film forming antioxidant significantly delays the oxidative detorioration of freeze-dried carrots as determined by smell and colour changes.

Example 3

Fresh ham was cut into slices of 3 mm thickness which were dipped in a 0.1% weight/weight dispersion of 6-0-Phytonoyl-L-ascorbic acid in distilled water for 1 minute at 4° C. A control was made by dipping fresh ham slices of the same size for the same time and temperature in the same amount of distilled water not containing any antioxidant.

The treated slices of ham were frozen and packed into plastic bags which were stored at $-20°$ C. for the periods of time shown in Table II below.

After storage, the slices of ham were evaluated by heating the treated samples at 150° C. for 10 minutes in a foil-covered pan with 5 ml of water added. The off-flavour caused by the oxidation of the fat was registered by smelling of the headspace gas and the results are shown in Table II.

TABLE II

| Storage time (days) | 3 | 40 | 160 |
|---|---|---|---|
| Example 1 | No off-flavour | Slight off-flavour | Off-flavour |
| Control | Slight off-flavour | Strong off-flavour | Strong off-flavour |

It can thus be seen that the treatment of ham with bilayer forming antioxidants slows down the development of rancid off-flavours.

I claim:

1. An antioxidant composition comprising a compound having the general formula:

$$CH_3\text{-}CH(CH_3)\text{-}CH_2\text{-}CH_2\text{-}CH_2\text{-}CH_2\text{-}CH(CH_3)\text{-}CH_2\text{-}CH_2\text{-}CH_2\text{-}CH_2\text{-}CH(CH_3)\text{-}CH_2\text{-}CH_2\text{-}CH_2\text{-}X\text{-}COOY$$

or salts thereof wherein X is selected from the group consisting of a methylene radical and an isopropylene radical and Y is a residue selected from the group consisting of a residue of L-ascorbic acid having the formula:

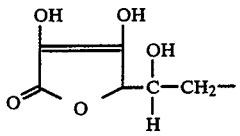

and a residue of D-isoascorbic acid having the formula:

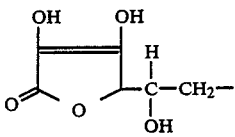

in an aqueous medium wherein sufficient water is present for inducing a lamellar liquid crystalline phase.

2. An antioxidant composition according to claim 1 wherein the water content of the aqueous medium is above 10% on a weight/weight basis.

3. An antioxidant composition according to claim 1 wherein the composition is a salt and wherein the water content of the aqueous medium is above 5% on a weight/weight basis.

4. An antioxidant composition according to claim 1 wherein the amount of the compound is from 0.01% to 1.0% by weight based on the total weight of the composition.

5. An antioxidant composition according to claim 4 wherein the amount of the compound is from 0.05% to 0.5% by weight based upon the total weight of the composition.

6. An antioxidant composition according to claim 1 wherein the salts are selected from the group consisting of alkali metal salts and alkaline earth metal salts.

7. An antioxidant composition according to claim 6 wherein the salts are selected from the group consisting of sodium, potassium, calcium and magnesium salts.

* * * * *

UNITED STATES PATENT AND TRADEMARK OFFICE
CERTIFICATE OF CORRECTION

PATENT NO. : 4,888,133

DATED : December 19, 1989

INVENTOR(S) : Thommy CARLSON

It is certified that error appears in the above-identified patent and that said Letters Patent is hereby corrected as shown below:

On the title page, item [54], "NEW ANTIOXIDANT SURFACTANTS" should be --ANTIOXIDANT SURFACTANTS--.

Column 2, line 50 of the specification, "antioxidation" should read --oxidation--.

Signed and Sealed this

Thirteenth Day of November, 1990

Attest:

HARRY F. MANBECK, JR.

*Attesting Officer*  *Commissioner of Patents and Trademarks*